United States Patent [19]

Tanaka et al.

[11] Patent Number: 5,003,113

[45] Date of Patent: Mar. 26, 1991

[54] PROCESS OF PRODUCING ISOPROPYLNAPHTHOLS

[75] Inventors: Michio Tanaka; Masayasu Ishibashi, both of Yamaguchi; Katsuo Taniguchi, Chiba, all of Japan

[73] Assignee: Mitsui Petrochemical Industries, Ltd., Tokyo, Japan

[21] Appl. No.: 440,212

[22] Filed: Nov. 22, 1989

[30] Foreign Application Priority Data

Nov. 25, 1988 [JP] Japan ................. 63-297828
Nov. 29, 1988 [JP] Japan ................. 63-301710

[51] Int. Cl.$^5$ ................. C07C 37/08; C07C 39/14
[52] U.S. Cl. ................. 568/736; 568/569
[58] Field of Search ............ 568/569, 577, 736, 737, 568/568

[56] References Cited

U.S. PATENT DOCUMENTS

| | | | |
|---|---|---|---|
| 2,771,491 | 11/1956 | Conner, Jr. ................. | 568/569 |
| 4,049,720 | 9/1977 | Hosaka et al. ................. | 568/569 |
| 4,503,262 | 3/1985 | Cupton et al. ................. | 568/569 |
| 4,906,790 | 3/1990 | Ishiguro et al. ................. | 568/736 |

FOREIGN PATENT DOCUMENTS

| | | | |
|---|---|---|---|
| 0320451 | 6/1989 | European Pat. Off. ............ | 568/736 |
| 2255442 | 11/1987 | Japan ................. | 568/569 |

*Primary Examiner*—Werren B. Lone
*Attorney, Agent, or Firm*—Sherman and Shalloway

[57] ABSTRACT

In a process of producing isopropylnaphthols by oxidizing diisopropylnaphthalenes with molecular oxygen in a liquid phase to provide a reaction mixture which contains therein diisopropylnaphthalene monohydroperoxides and then acid decomposing the monohydroperoxides to isopropylnaphthols, the improvement comprising separating an organic layer from the reaction mixture, adding lower aliphatic alcohols of 1-4 carbons to the organic layer, crystallizing the diisopropylnaphthalenes while allowing the diisopropylnaphthalene monohydroperoxides to remain dissolved in the lower aliphatic alcohols, thereby to separate the monohydroperoxides from the diisopropylnaphthalenes.

A further improvement in the process comprises crystallizing the isopropylnaphthols from aromatic hydrocarbons of 6–12 carbons.

8 Claims, No Drawings

PROCESS OF PRODUCING ISOPROPYLNAPHTHOLS

This invention relates to a process of producing isopropylnaphthols, more particularly, to a process of producing isopropylnaphthols by oxidizing diisopropylnaphthalenes with molecular oxygen in a liquid phase to produce diisopropylnaphthalene monohydroperoxides, and then by acid-decomposing the monohydroperoxides to isopropylnaphthols in high selectivities and in high yields.

Isopropylnaphthols such as 6-isopropyl-2-naphthol are useful as raw materials for the production of synthetic resins, synthetic fibers, medicines, agricultural chemicals or dyestuffs, as is well known. In general, 6-isopropyl-2-naphthol is produced by the oxidation of 2,6-diisopropylnaphthalene to 6-isopropyl-2-(2'-hydroperoxy-2'-propyl)-naphthalene (MHP), and the subsequent acid-decomposition of the monohydroperoxides with acid catalysts.

In U.S. Pat. No. 4,503,262, it is described that 2,6-diisopropylnaphthalene is oxidized with molecular oxygen to 2,6-diisopropylnaphthalene dihydroperoxides in organic solvents in the presence of heavy metal catalysts such as organic acid salts of cobalt, and that the use of aliphatic hydrocarbons of 5–14 carbons such as n-heptane as a solvent improves the oxidation rate, but also yield and purity of the dihydroperoxides. However, in the application of this process to the selective production of the 6-isopropyl-2-(2'-hydroperoxy-2'-propyl)naphthalene from 2,6-diisopropylnaphthalene, the reaction must be stopped at an initial stage, so that the conversion of the starting material and the yield of the desired monohydroperoxide are very low as well as much quantity of the raw material must be recovered.

Further, since the oxidation of diisopropylnaphthalenes proceeds stepwise similarly to the oxidation of diisopropyl-benzenes as is already known, and accordingly, it is very difficult to recover the monohydroperoxide in high yields from the reaction mixture.

A further process is already known, as is described in J. Am. Chem. Soc., 84, 284–292 (1962), in which $\beta$-isopropylnaphthalene is sulfonated at the 6-position with excess amounts of concentrated sulfuric acid to provide 2-isopropyl-6-naphthalenesulfonic acid, which is then hydrolyzed with large excess amounts of a potassium hydroxide solution, thereby to provide 6-isopropyl-2-naphthol. As will be apparent, the process needs large quantity of acids and alkalis, and is inevitably attended by a serious problem of waste water treating when being utilized in the commercial production of 6-isopropyl-2-naphthol.

A still further process is known, as is described in Japanese Patent Laid-Open No. 61-100558, in which the oxidation of diisopropylnaphthalenes is carried out in the presence of organic solvents such as chlorobenzene. However, the yield of the monohydroperoxide in the middle of the reaction is unsatisfactorily about 40 mol % based on the diisopropylnaphthalene used.

The oxidation of $\beta$-isopropylnaphthalene, a homologue of diisopropylnaphthalenes, with molecular oxygen in the presence of an aqueous alkaline solution to $\beta$-isopropylnaphthalene hydroperoxide is disclosed in Japanese Patent Laid-Open No. 51-34138 and British Patent No. 654,035. However, the oxidation of diisopropylnaphthalenes with molecular oxygen needs severer reaction conditions than in the oxidation of, for example, $\beta$-isopropylnaphthalene. When such severer reaction conditions are employed, the production of undesired naphthoquinones which inhibit the oxidation reaction increases, and therefore, it is infeasible to employ the oxidation process of $\beta$-isopropylnaphthalene as it is for the oxidation of diisopropylnaphthalenes.

It is also known that diisopropylbenzenes are oxidized to diisopropylbenzene dihydroperoxides, and the dihydroperoxide is decomposed in the presence of an acid catalyst to hydroquinone or resorcinol. However, the diisopropylnaphthalenes are different in the reactivity from p- or m-diisopropylbenzene, so that it is almost impossible to determine optimum reaction conditions of the oxidation of diisopropylnaphthalenes and the subsequent acid decomposition conditions on the ground of the known oxidation process of the diisopropylbenzenes.

As a further problem to be noted in the production of isopropylnaphthols, the acid-decomposition of the hydroperoxides provides a reaction mixture which contains a number of by-products such as acetylisopropylnaphthalenes, isopropenylisopropylnaphthalenes, acetone condensates or polymers, in addition to desired isopropylnaphthols. It is also difficult to recover the isopropylnaphthols in high yields from the reaction mixture.

The use of aliphatic hydrocarbons or mixtures of aliphatic hydrocarbons and lower aliphatic alcohols to crystallize the resultant isopropylnaphthols from the reaction mixture. However, the resultant isopropylnaphthols are still low in purity.

It is already known that dihydroxynaphthalenes are crystallized out by use of a mixture of water and aliphatic ketones of 3 or 4 carbons or a mixture of water and aliphatic alcohols of 1–5 carbons, as described in Japanese Patent Laid-open No. 63-39831. However, this method is applied to purification of isopropylnaphthols in vain since the isopropylnaphthols are different in properties from the dihydroxynaphthalenes. The reference further refers to the use of aromatic hydrocarbons as crystallizing solvents which results in recovery of dihydroxynaphthalene crystals of purity of as low as 20–60%.

Therefore, it is a general object of the invention to provide a process for producing isopropylnaphthols in higher purities and higher yields by oxidizing diisopropylnaphthalenes with molecular oxygen in a liquid phase to diisopropylnaphthalene monohydroperoxides and then by acid-decomposing the hydroperoxides than in the prior art.

It is a specific object of the invention to provide a process for producing isopropylnaphthols wherein the monohydroperoxides are recovered after the oxidation of diisopropylnaphthalenes to carry out the subsequent acid-decomposition thereof efficiently, thereby to improve the industrial productivity of the isopropylnaphthols.

It is a further specific object of the invention to provide a process for producing isopropylnaphthols wherein the isopropylnaphthols are recovered as high purity and colorless crystals from the reaction mixture after the acid-decomposition of the monohydroperoxides.

According to the invention, there is provided a process of producing isopropylnaphthols by oxidizing diisopropylnaphthalenes with molecular oxygen in a liquid phase to provide a reaction mixture which contains therein diisopropylnaphthalene monohydroperoxides and then acid-decomposing the monohydroperoxides to isopropylnaphthols, in which the improvement comprising separating an organic layer from the reaction mixture, adding lower aliphatic alcohols of 1-4 carbons to the organic layer, crystallizing the diisopropylnaphthalenes while allowing the diisopropylnaphthalene monohydroperoxides to remain dissolved in the lower aliphatic alcohols, thereby to separate the monohydroperoxides from the diisopropylnaphthalenes.

Further according to the invention, there is provided a process of producing isopropylnaphthols by the acid-decomposition of diisopropylnaphthalene monohydroperoxides, in which the improvement comprising crystallizing the resulting isopropylnaphthols from aromatic hydrocarbons of 6-12 carbons.

In the process of the invention, diisopropylnaphthalenes are first oxidized with molecular oxygen in a liquid phase in the presence of catalysts to provide a reaction mixture which contains therein diisopropylnaphthalene monohydroperoxides.

The diisopropylnaphthalenes used include, for example, 2,6-diisopropylnaphthalene, 2,7-diisopropylnaphthalene or 1,4-diisopropylnaphthalene, with the first most preferred.

There may be preferably used, as the catalyst, for example, alkali metal compounds such as sodium hydroxide, potassium hydroxide, sodium carbonate, potassium carbonate, sodium acetate, potassium acetate, sodium nitrate or potassium phosphate, alkaline earth metal compounds such as calcium hydroxide, magnesium hydroxide or strontium hydroxide, or noble metal catalysts such as palladium. Among these are preferred in particular potassium acetate, sodium acetate, potassium carbonate or sodium hydroxide. The catalysts may be used singly or as mixtures of two or more. They may be used as they are, but preferably as aqueous solutions of 3-50% by weight concentrations. The amount of the catalysts used is not specifically limited.

In the process of the invention, molecular oxygen is used singly or as a mixture with inert gases, and usually air is used. Although the amount of the molecular oxygen used is not specifically limited, but usually it is in the range of about 5-15 Nl/hour as oxygen in relation to 100 g of the diisopropylnaphthalenes used.

The oxidation reaction is effected usually at temperatures ranging from about 80° C. to about 150° C., preferably from about 90° C. to about 130° C., usually for a period of about 0.5-20 hours, preferably about 1-8 hours, although depending upon the other reaction conditions such as reaction temperatures. The reaction is usually carried out under normal or elevated pressures, preferably under elevated pressures of 5-15 Kg/cm$^2$G.

To carry out the oxidation reaction, the diisopropylnaphthalenes as an oil phase and aqueous solutions of the catalysts are first emulsified by fully admixing them mechanically. If necessary, emulsifiers such as stearic acid may be used. Then, gases containing molecular oxygen are blown into the emulsion under stirring to allow the resultant reaction mixture to remain emulsified.

The weight ratios of the oil phase to the aqueous phase in the reaction mixture are usually in the range of 0.2-20. When the ratio is more than 20, the mixtures of unreacted diisopropylnaphthalenes, their oxidation products and the aqueous solutions of catalysts are poorly emulsified, and this adversely affects the oxidation reaction. When the ratio is smaller than 0.2, the mixtures are likewise poorly emulsified. Further, it is preferred that the reaction is carried out at a small pH, usually in the range of 3-11, preferably in the range of 4-9.

The reaction under the conditions as above described provides diisopropylnaphthalene monohydroperoxides in high yields while the production of undesired diisopropylnaphthalene dihydroperoxides is effectively suppressed.

In the oxidation reaction of diisopropylnaphthalenes, the use of reaction initiator such as α, α'-azobis(cyclohexane-1-carbonitrile) is preferred to shorten the inductive period of the reaction. The amount of the initiator used is usually in the range of about 0.002-1 parts by weight per 100 parts by weight of the reaction mixture fed.

The oxidation of diisopropylnaphthalenes as set forth above provides diisopropylnaphthalene monohydroperoxides. When 2,6-diisopropylnaphthalene is used as a starting material, there are produced 6-isopropyl-2-(2'-hydroperoxy-2'-propyl)naphthalene (MHP), and in addition, as by-products, 2,6-diisopropylnaphthalene dihydroperoxide (DHP), 2-(2'-hydroxy-2'-propyl)-6-(2'-hydroperoxy-2'-propyl)naphthalene (HHP), 2,6-bis(2'-hydroxy-2'-propyl)naphthalene (DCA) and/or 6-isopropyl-2-(2'-hydroxy-2'-propyl)naphthalene (MCA).

The separation of diisopropylnaphthalene monohydroperoxides from the starting material or diisopropylnaphthalenes in accordance with the invention will now be described.

After the oxidation reaction, it is preferred that water-insoluble dialkyl ketones are first added to the reaction mixture, and then the mixture is separated into an aqueous layer and an organic oily layer. The reasons are as follows.

When the conversion rate has been raised to a significant degree, the resultant reaction mixture contains such hydroperoxides, in particular, 2,6-diisopropylnaphthalene dihydroperoxide, in large proportions as are liquid at the reaction temperature but solidify when the reaction mixture is cooled to room temperatures. When such dihydroperoxides produced are cooled, they incorporate thereinto the aqueous solution of the catalysts and solidify, so that it is difficult to remove the aqueous solution from the reaction mixture when the reaction mixture is cooled as it stands. Thus, the addition of water-insoluble dialkyl ketones to the reaction mixture after the oxidation reaction allows the reaction mixture to remain dissolved in the ketones, thereby to make the handling of the reaction mixture easy.

Dialkyl ketones of 5-10 carbons are preferred as the water-insoluble dialkyl ketones as above mentioned, and there may be specifically mentioned as such ketones, for example, methyl propyl ketone, methyl isobutyl ketone, diisopropyl ketone, ethyl isobutyl ketone, propyl butyl ketone, diisobutyl ketone or amyl butyl ketone, among these is preferred in particular methyl isobutyl ketone. The amount of the dialkyl ketones used is not specifically limited. The separated oily phase is then washed with water to remove aqueous phase therefrom.

The water-insoluble dialkyl ketones are then removed from the oily phase by, for example, distillation, and lower aliphatic alcohols of 1-4 carbons are added to the resultant concentrates, thereby to crystallize the diisopropylnaphthalenes, while alcohol-soluble diisopropylnaphthalene monohydroperoxide are allowed to remain dissolved in the alcohol.

The lower aliphatic alcohols of 1-4 carbons used include methanol, ethanol, propanol, butanol or mixtures of these. The alcohols are used preferably in amounts of 0.5-10 times in weight as much as the concentrates obtained.

The crystallized diisopropylnaphthalenes are removed by filtration or centrifugation from the mixture, and thus the diisopropylnaphthalene monohydroperoxide and the unreacted diisopropylnaphthalenes are separated from each other. The thus separated diisopropylnaphthalenes are of sufficient purity, usually not less than 70%, and are usable as they are as starting materials in the oxidation reaction.

Meanwhile, the alcohols are removed from the alcohol solution by, for example, distillation, and thus the resultant concentrates mainly contain the desired diisopropylnaphthalene monohydroperoxide, and only in small amounts of diisopropylnaphthalenes which have not been separated, diisopropylnaphthalene monocarbinols, diisopropylnaphthalene dihydroperoxides and the like. Therefore, the use of such concentrates makes it possible to employ small size reaction system in the consequent acid-decomposition thereof, but also render the purification of the resultant isopropylnaphthols easy.

As the final stage of the process, the diisopropylnaphthalene monohydroperoxide is acid-decomposed in the presence of acid catalysts to provide isopropylnaphthols. The acid catalyst used includes, for example, inorganic strong acids such as sulfuric acid, hydrochloric acid or phosphoric acid; a strongly acidic ion exchange resin; solid acids such as silica gel or silica-alumina; organic strong acids such as haloacetic acid, e.g., chloroacetic acid, alkanesulfonic acids, e.g., methanesulfonic acid or arenesulfonic acids, e.g., benzenesulfonic acid or p-toluenesulfonic acid; and heteropolyacids such as phosphorous tungstic acid or phosphorous molybdic acid; or "Nafion H". The acid catalyst is used usually in amounts of about 50 ppm to 1% by weight based on the total of the reaction mixture, although depending upon the catalyst used and the reaction conditions.

The acid-decomposition may be carried out in the presence of solvents such as toluene, methyl isobutyl ketone, acetonitrile or mixtures of these. The solvents may be used in amounts of 0.5-10 times in weight as much as the concentrates used.

Further, the acid-decomposition may be preferably carried out in the presence of hydrogen peroxide to oxidize diisopropylnaphthalene monocarbinols by-produced in the oxidation reaction to the monohydroperoxides, which are then decomposed to isopropylnaphthols in the presence of the acid catalyst, to increase the yield of isopropylnaphthols. The use of hydrogen peroxide has a further advantage to effectively prevent the by-production of condensates of diisopropylnaphthalene monocarbinols. Hydrogen peroxide is used in amounts usually of about 1-2 moles per mole of alcoholic hydroxyls of the aforesaid carbinols, to produce the desired isopropylnaphthols in high yields. Other substances such as sodium peroxide may also be used which produce hydrogen peroxide under the reaction conditions, in place of hydrogen peroxide.

The acid decomposition is carried out usually at temperatures of 0°-100° C., preferably of 20°-80° C., over a period of 0.05-3 hours, preferably of 0.1-2 hours.

The thus produced isopropylnaphthols are recovered and purified in manners which will now be described.

Alkaline solutions of such as sodium hydroxide, potassium hydroxide or sodium carbonate are added to the reaction mixture to neutralize the acid catalysts used. The resultant organic layer is washed with water, and there is added thereto aliphatic hydrocarbons of 8-13 carbons such as n-octane, n-nonane or n-decane. The mixture is then distilled to remove the solvents used, thereby to provide a slurry of crystallized isopropylnaphyhols in the aliphatic hydrocarbons.

The slurry is heated to dissolve the solid components therein, and then cooled usually to normal temperatures to crystallize isopropylnaphthols. The isopropylnaphthols are collected by filtration.

The recovery of isopropylnaphthols after the acid-decomposition may also be carried out in such manners as below described.

Alkaline solutions of such as sodium hydroxide, potassium hydroxide or sodium carbonate are added to the reaction mixture to neutralize the acid catalysts used. The resultant organic layer is separated and washed with water to remove water soluble components therefrom into an aqueous layer. The organic layer is then distilled to remove the solvents used, thereby to provide concentrates of the acid decomposition reaction products.

Then, if necessary, crude isopropylnaphthols are recovered from the concentrates by the following method. At first, lower aliphatic hydrocarbons or mixtures thereof with lower aliphatic alcohols are added to the concentrate. The mixture is then heated to dissolve the reaction products therein, and is then cooled usually to normal temperatures to crystallize the resultant isopropylnaphthols. The isopropylnaphthols are collected by filtration.

There may be used as the aliphatic hydrocarbons, for example, n-hexane, n-heptane, n-octane, n-nonane or n-decane, while there may be used as the lower aliphatic alcohol, for example, methanol or ethanol.

In accordance with the invention, aromatic hydrocarbons are added to the crude isopropylnaphthols thus recovered or the concentrates as before described, and the mixture is then heated preferably to 50°-120° C. to dissolve the isopropylnaphthols in the aromatic hydrocarbons, and then cooled preferably to normal temperatures, whereupon high purity isopropylnaphthols are crystallized out usually of more than 99% in purity. The crystallization may be effected repeatedly, when desired.

The aromatic hydrocarbons used are preferably of 6-12 carbons, and more specifically, there may be mentioned as such aromatic hydrocarbons, for example, benzene or alkylbenzenes such as toluene, xylene, trimethylbenzenes, cumene or diisopropylbenzenes. The aromatic hydrocarbons are used in amounts of 0.5-10 parts by weight per part by weight of the crude isopropylnaphthols or the concentrates.

The invention will now be more fully described with reference to examples, which however are not to be construed as limiting to the invention.

EXAMPLE 1

In a 15 liter capacity autoclave made from SUS provided with a stirrer, a cooling tube, a sampling opening, a gas inlet tube, a thermowell and a jacket were placed 3.0 Kg of 2,6-diisopropylnaphthalene, 6.0 Kg of a 5% aqueous potassium carbonate solution, palladium in amounts of 40 ppm based on 2,6-diisopropylnaphthalene, and 20 g of α, α'-azobis(cyclohexane-1-carbonitrile) as a polymerization initiator. Steam was supplied to the jacket to heat the mixture to 100° C. and the autoclave was pressurized to 5 kg/cm$^2$G with air, and then the oxidation was carried out under pressure for three hours while air was fed thereinto at a rate of 1 m$^3$ per hour.

After the completion of the reaction, 4 Kg of methyl isobutyl ketone was added to the reaction mixture to separate an organic layer from an aqueous layer. The organic layer was washed twice with one liter of water.

The organic layer was analyzed and was found that the conversion of 2,6-diisopropylnaphthalene was 21.6 mol % and the total oxidation rate to 6-isopropyl-2-(2'-hydroperoxy-2'-propyl)naphthalene (MHP) and 6-isopropyl-2-(2'-hydroxy-2'-propyl)naphthalene (MCA) was 93.0 mol %.

The organic layer was distilled to remove methyl isobutyl ketone, 2000 ml of methanol was added to the resultant concentrates. The mixture was heated to a solution and then cooled. An amount of 2402 g of crystals were obtained while 2646g of a mother liquor were obtained. The crystals were found to contain 92.3% by weight of 2,6-diisopropylnaphthalene, 7.5% by weight of MHP and 0.2% by weight of MCA. Thus, MHP was found to remain substantially in the mother liquor.

The solvent was removed from the mother liquor to provide 1372 g of concentrates. An amount of 628 g of methyl isobutyl ketone was added to the concentrate to provide a mixture as a feed material for acid decomposition.

In a five liter separable flask were placed 2 g of sulfuric acid and 2000 g of methyl isobutyl ketone, and the mixture was heated to 60° C. Then, to the mixture were added 2000 g of the above mentioned feed material and 2.9 g of 60% hydrogen peroxide aqueous solution diluted with 300 g of acetone was fed into the flask over one hour to carry out acid-decomposition. After the addition, the reaction was carried out for another 30 minutes.

After the completion of the reaction, the reaction mixture was neutralized, and acetone was removed therefrom with a rotary evaporator. Then the mixture was washed with water and the solvent was removed therefrom, to provide 1076 g of a reaction mixture. By the analysis of the reaction mixture by liquid chromatography, the mixture was found to contain 336 g of 2,6-diisopropylnaphthalene and 381 g of 6-isopropyl-2-naphthol. The acid decomposition yield was 95.0 mol %.

EXAMPLE 2

In a 15 liter capacity autoclave made from SUS provided with a stirrer, a cooling tube, a sampling opening, a gas inlet tube, a thermowell and a jacket were placed 3.0 Kg of 2,6-diisopropylnaphthalene, 6.0 Kg of a 5% aqueous potassium carbonate solution, palladium in amounts of 40 ppm based on 2,6-diisopropylnaphthalene, and 20 g of α, α'-azobis(cyclohexane-1-carbonitrile) as a polymerization initiator. Steam was supplied to the jacket to heat the mixture to 100° C. and the autoclave was pressurized to 5 kg/cm$^2$G with air, and then the oxidation was carried out under the pressure for three hours while air was fed thereinto at a rate of 1 m$^3$ per hour.

After the completion of the reaction, 4 Kg of methyl isobutyl ketone was added to the reaction mixture to separate an organic layer from an aqueous layer. The organic layer was washed twice with one liter of water.

The organic layer was analyzed and was found that the conversion of 2,6-diisopropylnaphthalene was 30.2 mol % and the yield of MHP was 25.7%.

The organic layer was distilled to remove methyl isobutyl ketone, and to the resultant concentrates an amount of 1600 ml of isopropanol was added. The mixture was heated to a solution and then cooled. An amount of 2420 g of crystals was obtained while 2364 g of a mother liquor was obtained. The crystals were found to contain 77.3% by weight of 2,6-diisopropylnaphthalene, 19.3% by weight of MHP, 0.8% by weight of MCA and 1.2% by weight of DHP. Thus, MHP was found to remain substantially in the mother liquor.

The solvent was removed from the mother liquor to provide 1307 g of concentrates. An amount of 603 g of methyl isobutyl ketone was added to the concentrate to provide a mixture as a feed material for acid-decomposition.

The concentrate was acid-decomposed in the same manner as in the Example 1, to provide 345 g of 6-isopropylnaphthol.

EXAMPLE 3

The acid-decomposition reaction product obtained in the Example 1 was crystallized from methanol and hexane to provide 206 g of crude 6-isopropyl-2-naphthol.

An amount of 700 g of toluene was added to the crude crystals and purified by crystallization therefrom to provide 130 g of white crystals of 6-isopropyl-2-naphthol having a purity of 99.7% by weight.

COMPARATIVE EXAMPLE 1

Crude crystals of 6-isopropyl-2-naphthol were produced in the same manner as in the Example 3. The crude crystals were pale brown and found to have a purity of 82.0% by weight before the crystallization from toluene.

EXAMPLE 4

Ethylbenzene was used in place of toluene, and otherwise in the same manner as in the Example 3, the crude crystals were purified, to provide 126 g of white crystals of 6-isopropyl-2-naphthol having a purity of 99.2% by weight.

EXAMPLE 5 p-Xylene was used in place of toluene, and otherwise in the same manner as in the Example 3, the crude crystals were purified, to provide 124 g of white crystals of 6-isopropyl-2-naphthol having a purity of 99.0% by weight.

EXAMPLE 6

Cumene was used in place of toluene, and otherwise in the same manner as in the Example 3, the crude crystals were purified, to provide 128 g of white crystals of 6-isopropyl-2-naphthol having a purity of 99.6% by weight.

What is claimed is:

1. In a process of producing isopropylnaphthols by oxidizing diisopropylnaphthalenes with molecular oxygen in a liquid phase at a temperature of 80°–150° C. under normal or elevated pressures to provide a reaction mixture which contains therein diisopropylnaphthalene monohydroperoxides and then acid-decomposing the monohydroperoxides to isopropylnaphthols at a temperature of 0°–100° C., the improvement comprising separating an organic layer from the reaction mixture, adding lower aliphatic alcohol of 1–4 carbons to the organic layer, crystallizing the diisopropylnaphthalenes while allowing the diisopropylnaphthalene monohydroperoxides to remain dissolved in the lower aliphatic alcohol, thereby to separate the monohydroperoxides from the diisopropylnaphthalenes.

2. The improvement as claimed in claim 1 wherein the lower aliphatic alcohol is selected from the group consisting of methanol, ethanol, propanol and butanol.

3. In a process of producing isopropylnaphthols by the acid-decomposition of diisopropylnaphthalene monohydroperoxides at a temperature of 0°–100° C., the improvement comprising crystallizing the isopropylnaphthols from aromatic hydrocarbon of 6–12 carbons.

4. The improvement as claimed in claim 3 wherein the aromatic hydrocarbon is selected from the group consisting of benzene and alkylbenzenes.

5. The improvement as claimed in claim 4 wherein the alkylbenzene is toluene, xylene, trimethylbenzene, cumene or diisopropylbenzene.

6. In a process of producing isopropylnaphthols by oxidizing diisopropylnaphthalenes with molecular oxygen in a liquid phase at a temperature of 80°–150° C. under normal or elevated pressures to provide a reaction mixture which contains therein diisopropylnaphthalene monohydroperoxides and then acid-decomposing the monohydroperoxides to isopropylnaphthols at a temperature of 0°–100° C., the improvement comprising crystallizing the isopropylnaphthols from aromatic hydrocarbon of 6–12 carbons.

7. The improvement as claimed in claim 6 wherein the aromatic hydrocarbon is selected from the group consisting of benzene and alkylbenzenes.

8. The improvement as claimed in claim 7 wherein the alkylbenzene is toluene, xylene, trimethylbenzene, cumene or diisopropylbenzene.

* * * * *